United States Patent
Sockness et al.

(10) Patent No.: US 9,018,488 B2
(45) Date of Patent: Apr. 28, 2015

(54) PLANTS AND SEEDS OF CORN VARIETY CV113991

(71) Applicant: Monsanto Technology LLC, St. Louis, MO (US)

(72) Inventors: Bradley A. Sockness, Owatonna, MN (US); Scott A. Bergemann, Northfield, MN (US)

(73) Assignee: Monsanto Technology LLC, St. Louis, MO (US)

( * ) Notice: Subject to any disclaimer, the term of this patent is extended or adjusted under 35 U.S.C. 154(b) by 119 days.

(21) Appl. No.: 13/889,540

(22) Filed: May 8, 2013

(65) Prior Publication Data
US 2014/0338055 A1 Nov. 13, 2014

(51) Int. Cl.
*A01H 5/10* (2006.01)
*C12N 5/04* (2006.01)
*C12N 15/82* (2006.01)

(52) U.S. Cl.
CPC ............ *A01H 5/10* (2013.01); *C12N 15/8241* (2013.01); *C12N 15/8245* (2013.01); *C12N 15/8247* (2013.01); *C12N 15/8251* (2013.01); *C12N 15/8274* (2013.01); *C12N 15/8275* (2013.01); *C12N 15/8278* (2013.01); *C12N 15/8279* (2013.01); *C12N 15/8286* (2013.01); *C12N 15/8289* (2013.01); *C12N 5/04* (2013.01)

(58) Field of Classification Search
USPC ...................................................... 800/320.1
See application file for complete search history.

(56) References Cited

U.S. PATENT DOCUMENTS

| | | | |
|---|---|---|---|
| 4,658,085 | A | 4/1987 | Beversdorf et al. |
| 5,523,520 | A | 6/1996 | Hunsperger et al. |
| 5,773,683 | A | 6/1998 | Foley |
| 6,433,261 | B2 | 8/2002 | Hotchkiss |
| 6,693,232 | B1 | 2/2004 | Bergemann |
| 6,852,915 | B2 | 2/2005 | Johnson |
| 7,321,087 | B1 | 1/2008 | Carlson |
| 7,351,888 | B1 | 4/2008 | Peters |
| 8,722,997 | B2 * | 5/2014 | Boerboom ................. 800/320.1 |

OTHER PUBLICATIONS

U.S. Appl. No. 13/903,903, filed May 28, 2013, Bergemann et al.
Eshed et al., "Less-than-additive epistatic interactions of quantitative trait loci in tomato," *Genetic*, 143:1807-1817, 1996.
Fehr (ed.), In: Principles of Cultivar Development, vol. 1: Theory and Technique, pp. 360-376, 1987.
Hallauer et al., "Corn breeding," In: Corn and Corn Improvement, Sprague et al. (Eds.), Madison, Wisconsin, Ch. 8, pp. 463-564, 1988.
Kraft et al., "Linkage disequilibrium and fingerprinting in sugar beet," *Theor Appl Genet*, 101:323-326, 2000.
Krakowsky et al., "Quantitative trait loci for cell wall components in recombinant inbred lines of maize (*Zea mays* L.) II: leaf sheath tissue," *Theor Appl Genet* 112:717-726, 2006.
Larson et al., "Corn Production," In: Corn and Corn Improvement, G.F. Sprague (Ed.), No. 18 in Agronomy Series, American Society of Agronomy, Inc., Madison, Wisconsin, pp. 625-669, 1977.
Meghji et al., "Inbreeding depression, inbred and hybrid grain yields, and other traits of maize genotypes representing three eras," *Crop Science*, 24:545-549, 1984.
Sprague et al., "Corn Breeding," In: Corn and Corn Improvements, G.F. Sprague (Ed.), No. 18 in Agronomy Series, American Society of Agronomy, Inc., Madison, Wisconsin, pp. 305-362, 1977.
Wych, "Production of hybrid seed corn," In: Corn and Corn Improvement, Sprague et al. (Eds.), Madison, Wisconsin, Ch. 9, pp. 565-607, 1988.
Variety specific information as indicated in transmittal letter of Aug. 14, 2013 Information Disclosure Statement for U.S. Appl. No. 13/889,540.

* cited by examiner

*Primary Examiner* — Medina A Ibrahim
(74) *Attorney, Agent, or Firm* — Dentons US LLP

(57) ABSTRACT

According to the invention, there is provided seed and plants of the corn variety designated CV113991. The invention thus relates to the plants, seeds and tissue cultures of the variety CV113991, and to methods for producing a corn plant produced by crossing a corn plant of variety CV113991 with itself or with another corn plant, such as a plant of another variety. The invention further relates to corn seeds and plants produced by crossing plants of variety CV113991 with plants of another variety, such as another inbred line. The invention further relates to the inbred and hybrid genetic complements of plants of variety CV113991.

20 Claims, No Drawings

PLANTS AND SEEDS OF CORN VARIETY CV113991

BACKGROUND OF THE INVENTION

1. Field of the Invention

The present invention relates generally to the field of corn breeding. In particular, the invention relates to corn seed and plants of the variety designated CV113991, and derivatives and tissue cultures thereof.

2. Description of Related Art

The goal of field crop breeding is to combine various desirable traits in a single variety/hybrid. Such desirable traits include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Breeding techniques take advantage of a plant's method of pollination. There are two general methods of pollination: a plant self-pollinates if pollen from one flower is transferred to the same or another flower of the same plant. A plant cross-pollinates if pollen comes to it from a flower on a different plant.

Corn plants (*Zea mays* L.) can be bred by both self-pollination and cross-pollination. Both types of pollination involve the corn plant's flowers. Corn has separate male and female flowers on the same plant, located on the tassel and the ear, respectively. Natural pollination occurs in corn when wind blows pollen from the tassels to the silks that protrude from the tops of the ear shoot.

Plants that have been self-pollinated and selected for type over many generations become homozygous at almost all gene loci and produce a uniform population of true breeding progeny, a homozygous plant. A cross between two such homozygous plants produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform corn plant hybrids requires the development of homozygous inbred plants, the crossing of these inbred plants, and the evaluation of the crosses. Pedigree breeding and recurrent selection are examples of breeding methods used to develop inbred plants from breeding populations. Those breeding methods combine the genetic backgrounds from two or more inbred plants or various other broad-based sources into breeding pools from which new inbred plants are developed by selfing and selection of desired phenotypes. The new inbreds are crossed with other inbred plants and the hybrids from these crosses are evaluated to determine which of those have commercial potential.

North American farmers plant tens of millions of acres of corn at the present time and there are extensive national and international commercial corn breeding programs. A continuing goal of these corn breeding programs is to develop corn hybrids that are based on stable inbred plants and have one or more desirable characteristics. To accomplish this goal, the corn breeder must select and develop superior inbred parental plants.

SUMMARY OF THE INVENTION

In one aspect, the present invention provides a corn plant of the variety designated CV113991. Also provided are corn plants having all the physiological and morphological characteristics of the inbred corn variety CV113991. The inbred corn plant of the invention may further comprise, or have, a cytoplasmic or nuclear factor that is capable of conferring male sterility or otherwise preventing self-pollination, such as by self-incompatibility. Parts of the corn plant of the present invention are also provided, for example, pollen obtained from an inbred plant and an ovule of the inbred plant.

The invention also concerns seed of the inbred corn variety CV113991. The inbred corn seed of the invention may be provided as an essentially homogeneous population of inbred corn seed of the variety designated CV113991. Essentially homogeneous populations of inbred seed are generally free from substantial numbers of other seed. Therefore, in the practice of the present invention, inbred seed generally forms at least about 97% of the total seed. The population of inbred corn seed of the invention may be particularly defined as being essentially free from hybrid seed. The inbred seed population may be separately grown to provide an essentially homogeneous population of inbred corn plants designated CV113991.

In a further aspect of the invention, a composition is provided comprising a seed of corn variety CV113991 comprised in plant seed growth media. In certain embodiments, the plant seed growth media is a soil or synthetic cultivation medium. In specific embodiments, the growth medium may be comprised in a container or may, for example, be soil in a field.

In another aspect of the invention, a plant of corn variety CV113991 comprising an added heritable trait is provided. The heritable trait may comprise a genetic locus that is a dominant or recessive allele. In one embodiment of the invention, a plant of corn variety CV113991 comprising a single locus conversion in particular is provided. In specific embodiments of the invention, an added genetic locus confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring maize gene introduced into the genome of the variety by backcrossing, a natural or induced mutation, or a transgene introduced through genetic transformation techniques. When introduced through transformation, a genetic locus may comprise one or more transgenes integrated at a single chromosomal location.

In yet another aspect of the invention, an inbred corn plant of the variety designated CV113991 is provided, wherein a cytoplasmically-inherited trait has been introduced into said inbred plant. Such cytoplasmically-inherited traits are passed to progeny through the female parent in a particular cross. An exemplary cytoplasmically-inherited trait is the male sterility trait. Cytoplasmic-male sterility (CMS) is a pollen abortion phenomenon determined by the interaction between the genes in the cytoplasm and the nucleus. Alteration in the mitochondrial genome and the lack of restorer genes in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus, and continue to be male sterile in the next generation. The male fertility of a CMS plant can be restored by a restorer version of the same variety, which must have the restorer gene(s) in the nucleus. With the restorer gene(s) in the nucleus, the offspring of the male-sterile plant can produce normal pollen grains and propagate. A cytoplasmically inherited trait may be a naturally occurring maize trait or a trait introduced through genetic transformation techniques.

In another aspect of the invention, a tissue culture of regenerable cells of a plant of variety CV113991 is provided. The tissue culture will preferably be capable of regenerating plants capable of expressing all of the physiological and morphological characteristics of the variety, and of regenerating plants having substantially the same genotype as other plants of the variety. Examples of some of the physiological and morphological characteristics that may be assessed include characteristics related to yield, maturity, and kernel quality. The regenerable cells in such tissue cultures will preferably be derived from embryos, meristematic cells, immature tassels, microspores, pollen, leaves, anthers, roots, root tips, silk, flowers, kernels, ears, cobs, husks, or stalks, or from callus or protoplasts derived from those tissues. Still further, the present invention provides corn plants regenerated from the tissue cultures of the invention, the plants having all the physiological and morphological characteristics of variety CV113991.

In yet another aspect of the invention, processes are provided for producing corn seeds or plants, which processes generally comprise crossing a first parent corn plant as a male or female parent with a second parent corn plant, wherein at least one of the first or second parent corn plants is a plant of the variety designated CV113991. These processes may be further exemplified as processes for preparing hybrid corn seed or plants, wherein a first inbred corn plant is crossed with a second corn plant of a different, distinct variety to provide a hybrid that has, as one of its parents, the inbred corn plant variety CV113991. In these processes, crossing will result in the production of seed. The seed production occurs regardless of whether the seed is collected or not.

In one embodiment of the invention, the first step in "crossing" comprises planting, preferably in pollinating proximity, seeds of a first and second parent corn plant, and preferably, seeds of a first inbred corn plant and a second, distinct inbred corn plant. Where the plants are not in pollinating proximity, pollination can nevertheless be accomplished by transferring a pollen or tassel bag from one plant to the other as described below.

A second step comprises cultivating or growing the seeds of said first and second parent corn plants into plants that bear flowers (corn bears both male flowers (tassels) and female flowers (silks) in separate anatomical structures on the same plant). A third step comprises preventing self-pollination of the plants, i.e., preventing the silks of a plant from being fertilized by any plant of the same variety, including the same plant. This is preferably done by emasculating the male flowers of the first or second parent corn plant, (i.e., treating or manipulating the flowers so as to prevent pollen production, in order to produce an emasculated parent corn plant). Self-incompatibility systems may also be used in some hybrid crops for the same purpose. Self-incompatible plants still shed viable pollen and can pollinate plants of other varieties but are incapable of pollinating themselves or other plants of the same variety.

A fourth step may comprise allowing cross-pollination to occur between the first and second parent corn plants. When the plants are not in pollinating proximity, this is done by placing a bag, usually paper or glassine, over the tassels of the first plant and another bag over the silks of the incipient ear on the second plant. The bags are left in place for at least 24 hours. Since pollen is viable for less than 24 hours, this assures that the silks are not pollinated from other pollen sources, that any stray pollen on the tassels of the first plant is dead, and that the only pollen transferred comes from the first plant. The pollen bag over the tassel of the first plant is then shaken vigorously to enhance release of pollen from the tassels, and the shoot bag is removed from the silks of the incipient ear on the second plant. Finally, the pollen bag is removed from the tassel of the first plant and is placed over the silks of the incipient ear of the second plant, shaken again and left in place. Yet another step comprises harvesting the seeds from at least one of the parent corn plants. The harvested seed can be grown to produce a corn plant or hybrid corn plant.

The present invention also provides corn seed and plants produced by a process that comprises crossing a first parent corn plant with a second parent corn plant, wherein at least one of the first or second parent corn plants is a plant of the variety designated CV113991. In one embodiment of the invention, corn seed and plants produced by the process are first generation ($F_1$) hybrid corn seed and plants produced by crossing an inbred in accordance with the invention with another, distinct inbred. The present invention further contemplates seed of an $F_1$ hybrid corn plant. Therefore, certain exemplary embodiments of the invention provide an $F_1$ hybrid corn plant and seed thereof.

In still yet another aspect of the invention, the genetic complement of the corn plant variety designated CV113991 is provided. The phrase "genetic complement" is used to refer to the aggregate of nucleotide sequences, the expression of which sequences defines the phenotype of, in the present case, a corn plant, or a cell or tissue of that plant. A genetic complement thus represents the genetic make up of an inbred cell, tissue or plant, and a hybrid genetic complement represents the genetic make up of a hybrid cell, tissue or plant. The invention thus provides corn plant cells that have a genetic complement in accordance with the inbred corn plant cells disclosed herein, and plants, seeds and diploid plants containing such cells.

Plant genetic complements may be assessed by genetic marker profiles, and by the expression of phenotypic traits that are characteristic of the expression of the genetic complement, e.g., isozyme typing profiles. It is understood that variety CV113991 could be identified by any of the many well known techniques such as, for example, Simple Sequence Length Polymorphisms (SSLPs) (Williams et al., *Nucleic Acids Res.*, 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

In still yet another aspect, the present invention provides hybrid genetic complements, as represented by corn plant cells, tissues, plants, and seeds, formed by the combination of a haploid genetic complement of an inbred corn plant of the invention with a haploid genetic complement of a second corn plant, preferably, another, distinct inbred corn plant. In another aspect, the present invention provides a corn plant regenerated from a tissue culture that comprises a hybrid genetic complement of this invention.

In still yet another aspect, the present invention provides a method of producing an inbred corn plant derived from the corn variety CV113991, the method comprising the steps of: (a) preparing a progeny plant derived from corn variety CV113991, wherein said preparing comprises crossing a plant of the corn variety CV113991 with a second corn plant; (b) crossing the progeny plant with itself or a second plant to produce a seed of a progeny plant of a subsequent generation; (c) growing a progeny plant of a subsequent generation from said seed of a progeny plant of a subsequent generation and crossing the progeny plant of a subsequent generation with itself or a second plant; and (d) repeating the steps for an additional 3-10 generations to produce an inbred corn plant derived from the corn variety CV113991. In the method, it may be desirable to select particular plants resulting from step (c) for continued crossing according to steps (b) and (c). By selecting plants having one or more desirable traits, an inbred corn plant derived from the corn variety CV113991 is obtained which possesses some of the desirable traits of corn variety CV113991 as well as potentially other selected traits.

DETAILED DESCRIPTION OF THE INVENTION

I. Definitions of Plant Characteristics

Barren Plants: Plants that are barren, i.e., lack an ear with grain, or have an ear with only a few scattered kernels.

Cg: *Colletotrichum graminicola* rating. Rating times 10 is approximately equal to percent total plant infection.

CLN: Corn Lethal Necrosis (combination of Maize Chlorotic Mottle Virus and Maize Dwarf Mosaic virus) rating: numerical ratings are based on a severity scale where 1=most resistant to 9=susceptible.

Cn: *Corynebacterium nebraskense* rating. Rating times 10 is approximately equal to percent total plant infection.

Cz: *Cercospora zeae-maydis* rating. Rating times 10 is approximately equal to percent total plant infection.

Dgg: *Diatraea grandiosella* girdling rating (values are percent plants girdled and stalk lodged).

Dropped Ears: Ears that have fallen from the plant to the ground.

Dsp: *Diabrotica* species root ratings (1=least affected to 9=severe pruning).

Ear-Attitude: The attitude or position of the ear at harvest scored as upright, horizontal, or pendant.

Ear-Cob Color: The color of the cob, scored as white, pink, red, or brown.

Ear-Cob Diameter: The average diameter of the cob measured at the midpoint.

Ear-Cob Strength: A measure of mechanical strength of the cobs to breakage, scored as strong or weak.

Ear-Diameter: The average diameter of the ear at its midpoint.

Ear-Dry Husk Color: The color of the husks at harvest scored as buff, red, or purple.

Ear-Fresh Husk Color: The color of the husks 1 to 2 weeks after pollination scored as green, red, or purple.

Ear-Husk Bract: The length of an average husk leaf scored as short, medium, or long.

Ear-Husk Cover: The average distance from the tip of the ear to the tip of the husks. Minimum value no less than zero.

Ear-Husk Opening: An evaluation of husk tightness at harvest scored as tight, intermediate, or open.

Ear-Length: The average length of the ear.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the sum of the shelled grain weight and cob weight for a single ear.

Ear-Silk Color: The color of the silk observed 2 to 3 days after silk emergence scored as green-yellow, yellow, pink, red, or purple.

Ear-Taper (Shape): The taper or shape of the ear scored as conical, semi-conical, or cylindrical.

Ear-Weight: The average weight of an ear.

Early Stand: The percent of plants that emerge from the ground as determined in the early spring.

ER: Ear rot rating (values approximate percent ear rotted).

Final Stand Count: The number of plants just prior to harvest.

GDUs: Growing degree units which are calculated by the Barger Method, where the heat units for a 24-h period are calculated as GDUs=[(Maximum daily temperature+Minimum daily temperature)/2]−50. The highest maximum daily temperature used is 86° F. and the lowest minimum temperature used is 50° F.

GDUs to Shed: The number of growing degree units (GDUs) or heat units required for an inbred line or hybrid to have approximately 50% of the plants shedding pollen as measured from time of planting. GDUs to shed is determined by summing the individual GDU daily values from the planting date to the date of 50% pollen shed.

GDUs to Silk: The number of growing degree units for an inbred line or hybrid to have approximately 50% of the plants with silk emergence as measured from the time of planting. GDUs to silk is determined by summing the individual GDU daily values from the planting date to the date of 50% silking.

Hc2: *Helminthosporium carbonum* race 2 rating. Rating times 10 is approximately equal to percent total plant infection.

Hc3: *Helminthosporium carbonum* race 3 rating. Rating times 10 is approximately equal to percent total plant infection.

Hm: *Helminthosporium maydis* race 0 rating. Rating times 10 is approximately equal to percent total plant infection.

Ht1: *Helminthosporium turcicum* race 1 rating. Rating times 10 is approximately equal to percent total plant infection.

Ht2: *Helminthosporium turcicum* race 2 rating. Rating times 10 is approximately equal to percent total plant infection.

HtG: Chlorotic-lesion type resistance. +=indicates the presence of Ht chlorotic-lesion type resistance; −=indicates absence of Ht chlorotic-lesion type resistance; and +/−=indicates segregation of Ht chlorotic-lesion type resistance. Rating times 10 is approximately equal to percent total plant infection.

Kernel-Aleurone Color: The color of the aleurone scored as white, pink, tan, brown, bronze, red, purple, pale purple, colorless, or variegated.

Kernel-Cap Color: The color of the kernel cap observed at dry stage, scored as white, lemon-yellow, yellow, or orange.

Kernel-Endosperm Color: The color of the endosperm scored as white, pale yellow, or yellow.

Kernel-Endosperm Type: The type of endosperm scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp scored as colorless, red-white crown, tan, bronze, brown, light red, cherry red, or variegated.

Kernel-Row Direction: The direction of the kernel rows on the ear scored as straight, slightly curved, spiral, or indistinct (scattered).

Kernel-Row Number: The average number of rows of kernels on a single ear.

Kernel-Side Color: The color of the kernel side observed at the dry stage, scored as white, pale yellow, yellow, orange, red, or brown.

Kernel-Thickness: The distance across the narrow side of the kernel.

Kernel-Type: The type of kernel scored as dent, flint, or intermediate.

Kernel-Weight: The average weight of a predetermined number of kernels.

Kernel-Width: The distance across the flat side of the kernel.

Kz: *Kabatiella zeae* rating. Rating times 10 is approximately equal to percent total plant infection.

Leaf-Angle: Angle of the upper leaves to the stalk scored as upright (0 to 30 degrees), intermediate (30 to 60 degrees), or lax (60 to 90 degrees).

Leaf-Color: The color of the leaves 1 to 2 weeks after pollination scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal Waves: A rating of the waviness of the leaf margin 1 to 2 weeks after pollination. Rated as none, few, or many.

Leaf-Number: The average number of leaves of a mature plant. Counting begins with the cotyledonary leaf and ends with the flag leaf.

Leaf-Sheath Anthocyanin: A rating of the level of anthocyanin in the leaf sheath 1 to 2 weeks after pollination, scored as absent, basal-weak, basal-strong, weak or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf measured at its widest point.

LSS: Late season standability (values times 10 approximate percent plants lodged in disease evaluation plots).

Moisture: The moisture of the grain at harvest.

On1: *Ostrinia nubilalis* 1st brood rating (1=resistant to 9=susceptible).

On2: *Ostrinia nubilalis* 2nd brood rating (1=resistant to 9=susceptible).

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Root Lodging: Root lodging is the percentage of plants that root lodge. A plant is counted as root lodged if a portion of the plant leans from the vertical axis by approximately 30 degrees or more.

Seedling Color: Color of leaves at the 6 to 8 leaf stage.

Seedling Height: Plant height at the 6 to 8 leaf stage.

Seedling Vigor: A visual rating of the amount of vegetative growth on a 1 to 9 scale, where 1 equals best. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Sr: *Sphacelotheca reiliana* rating is actual percent infection.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk Lodging: The percentage of plants that did stalk lodge. Plants are counted as stalk lodged if the plant is broken over or off below the ear.

Stalk-Nodes With Brace Roots: The average number of nodes having brace roots per plant.

Stalk-Plant Height: The average height of the plant as measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity). It is usually recorded at the time the ear husks of most entries within a trial have turned a mature color. Scoring is on a 1 to 9 basis where 1 equals best.

STR: Stalk rot rating (values represent severity rating of 1=25% of inoculated internode rotted to 9=entire stalk rotted and collapsed).

SVC: Southeastern Virus Complex (combination of Maize Chlorotic Dwarf Virus and Maize Dwarf Mosaic Virus) rating; numerical ratings are based on a severity scale where 1=most resistant to 9=susceptible.

Tassel-Anther Color: The color of the anthers at 50% pollen shed scored as green-yellow, yellow, pink, red, or purple.

Tassel-Attitude: The attitude of the tassel after pollination scored as open or compact.

Tassel-Branch Angle: The angle of an average tassel branch to the main stem of the tassel scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume scored as present or absent.

Tassel-Glume Color: The color of the glumes at 50% shed scored as green, red, or purple.

Tassel-Length: The length of the tassel measured from the base of the bottom tassel branch to the tassel tip.

Tassel-Peduncle Length: The average length of the tassel peduncle, measured from the base of the flag leaf to the base of the bottom tassel branch.

Tassel-Pollen Shed: A visual rating of pollen shed determined by tapping the tassel and observing the pollen flow of approximately five plants per entry. Rated on a 1 to 9 scale where 9=sterile, 1=most pollen.

Tassel-Spike Length: The length of the spike measured from the base of the top tassel branch to the tassel tip.

Test Weight: Weight of the grain in pounds for a given volume (bushel) adjusted to 15.5% moisture.

Yield: Yield of grain at harvest adjusted to 15.5% moisture.

II. Other Definitions

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid ($F_1$) with one of the parental genotypes of the $F_1$ hybrid.

Chromatography: A technique wherein a mixture of dissolved substances are bound to a solid support followed by passing a column of fluid across the solid support and varying the composition of the fluid. The components of the mixture are separated by selective elution.

Crossing: The pollination of a female flower of a corn plant, thereby resulting in the production of seed from the flower.

Cross-pollination: Fertilization by the union of two gametes from different plants.

Diploid: A cell or organism having two sets of chromosomes.

Emasculate: The removal of plant male sex organs or the inactivation of the organs with a chemical agent or a cytoplasmic or nuclear genetic factor conferring male sterility.

$F_1$ Hybrid: The first generation progeny of the cross of two plants.

Genetic Complement: An aggregate of nucleotide sequences, the expression of which sequences defines the phenotype in corn plants, or components of plants including cells or tissue.

Genotype: The genetic constitution of a cell or organism.

Haploid: A cell or organism having one set of the two sets of chromosomes in a diploid.

Isozymes: Detectable variants of an enzyme, the variants catalyzing the same reaction(s) but differing from each other, e.g., in primary structure and/or electrophoretic mobility. The differences between isozymes are under single gene, codominant control. Consequently, electrophoretic separation to produce band patterns can be equated to different alleles at the DNA level. Structural differences that do not alter charge cannot be detected by this method.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Genetic loci that contribute, at least in part, certain numerically representable traits that are usually continuously distributed.

Regeneration: The development of a plant from tissue culture.

SSR profile: A profile of simple sequence repeats used as genetic markers and scored by gel electrophoresis following PCR™ amplification using flanking oligonucleotide primers.

Self-pollination: The transfer of pollen from the anther to the stigma of the same plant.

Single Locus Converted (Conversion) Plant: Plants which are developed by a plant breeding technique called backcrossing wherein essentially all of the desired morphological and physiological characteristics of an inbred are recovered in addition to the characteristics conferred by the single locus transferred into the inbred via the backcrossing technique.

Tissue Culture: A composition comprising isolated cells of the same or a different type or a collection of such cells organized into parts of a plant.

Transgene: A genetic sequence which has been introduced into the nuclear or chloroplast genome of a maize plant by a genetic transformation technique.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

III. Inbred Corn Plant CV113991

A. Origin and Breeding History

Inbred plant CV113991 was derived from a cross between the lines 1208993 and 1226218. The origin and breeding history of inbred plant CV113991 can be summarized as follows:

| | |
|---|---|
| Fall 2003 | The inbred line I208993 (a proprietary Monsanto inbred) was used as the pollen parent and crossed to the inbred line I226218 (a proprietary Monsanto inbred). The cross was made in Puerto Rico nursery field 05 PR ISIS03I41KLA. I208993 was located in Range 00006:Column 00001 and I226218 was located in Range 00006:Column 00004. |
| Winter 2004 | The F1 seed was grown, used as a female, and crossed to inbred line I285291 (a proprietary Monsanto inbred). The F1 was located in Puerto Rico nursery field 17 PR ISISI04U3SC; Range 00012:Column 00002. I285291 was located in Range 00012:Column 00001. The resulting F1 three-way seed was bulked. |
| Summer 2004 | The three way F1 seed was grown in a multiple row block in Owatonna nursery 17 17 MNOWM-03 starting in Range 00034:Column 00011. F2 ear 0006 was selected for advancement. |
| Summer 2006 | F2 ear 0006 was grown and self pollinated in Owatonna nursery 17 17 MNOWX-OW1; Range 00029:Column 00042. F3 ear 0002 was selected for advancement. |
| Summer 2007 | F3 ear 0002 was grown ear-to-row and self pollinated in Hawaii nursery field 17 40 HIKIK17-3W-SS; Range 00024:Column 00080. F4 ear 0001 was selected for advancement. |
| Winter 2007-08 | F4 ear 0001 was grown ear-to-row and self-pollinated in Chile |

-continued

| | |
|---|---|
| | nursery field AC 1C LIRAN3B; Range 00036:Column 00054. F5 ear 0003 was selected for advancement. |
| Summer 2008 | F5 ear 0003 was grown ear-to-row and self-pollinated in Stanton, MN nursery field AC 4T MNSTN06; Range 00022:Column 00037. Three ears were selected, and F6 ear 0003 was advanced as Breeder Seed. |
| Winter 2008-09 | F6 ear 0003 was grown ear-to-row and self-pollinated in Chile nursery AC 1C LIRAGRW1; Range 00014:Column 00314. Fourteen ears were selected and F7 ear 0015 was advanced as Breeder Seed. |
| Summer 2009 | F7 ear 0015 was grown ear-to-row and self-pollinated in Stanton, MN nursery BG 4T MNSTN04; Range 00007:Column 00049. Twenty ears were selected and F8 ear 0002 was advanced as Breeder Seed. The F5 generation was coded/finished as inbred CV113991. |
| Summer 2010 | F8 ear 0002 was grown ear-to-row and self-pollinated in Stanton, MN nursery BG 4T MNSTN05; Range 00019:Column 00014. Fifty-five ears were selected and F9 ear 0004 was advanced as Breeder Seed. |
| Summer 2011 | F9 ear 0004 was grown ear-to-row and self-pollinated in Stanton, MN nursery BG 4T MNSTN04; Range 00006:Column 00015. Final selection was made and seed from F10 ear 0001 was designated as Breeder Seed while the remaining ears were bulked. |

Corn variety CV113991 shows uniformity and stability within the limits of environmental influence for the traits described hereinafter in Table 1. CV113991 has been self-pollinated and ear-rowed a sufficient number of generations with careful attention paid to uniformity of plant type to ensure homozygosity and phenotypic stability. No variant traits have been observed or are expected in CV113991.

Inbred corn plants can be reproduced by planting the seeds of the inbred corn plant CV113991, growing the resulting corn plants under self-pollinating or sib-pollinating conditions with adequate isolation using standard techniques well known to an artisan skilled in the agricultural arts. Seeds can be harvested from such a plant using standard, well known procedures.

B. Phenotypic Description

In accordance with another aspect of the present invention, there is provided a corn plant having the physiological and morphological characteristics of corn plant CV113991. A description of the physiological and morphological characteristics of corn plant CV113991 is presented in Table 1.

TABLE 1

Physiological and Morphological Traits for Corn Variety CV113991

| | VALUE | | |
|---|---|---|---|
| CHARACTERISTIC | CV113991 | I226218 | I285291 |
| 1. STALK | | | |
| Plant Height (cm.) | 170.0 | 217.5 | 158.1 |
| Ear Height (cm) | 57.4 | 78.3 | 64.9 |
| Anthocyanin | Basal Weak | Absent | Absent |
| Brace Root Color | Faint | Absent | Faint |
| Internode Direction | Straight | Straight | Straight |
| Internode Length cm. | 12.4 | 17.0 | 12.6 |
| 2. LEAF | | | |
| Color | Dark Green | Green | Green |
| Length cm. | 62.7 | 83.3 | 54.1 |
| Width cm. | 7.9 | 10.5 | 7.5 |
| Sheath Anthocyanin | Absent | Absent | Absent |
| Sheath Pubescence | Light | Light | Heavy |
| Marginal Waves | Few | Moderate | Few |
| Longitudinal Creases | Moderate | Moderate | Moderate |
| 3. TASSEL | | | |
| Length cm. | 35.6 | 40.2 | 28.9 |
| Tassel Spike Length | 19.1 | 20.2 | 17.7 |
| Peduncle Length cm. | 6.9 | 7.4 | 1.8 |
| Branch Number | 11.7 | 7.7 | 8.0 |
| Anther Color | Yellow | Yellow | Yellow |
| Glume Color | Green | Pale Purple | Light Red |
| Glume Band | Absent | Absent | Absent |

TABLE 1-continued

Physiological and Morphological Traits for Corn Variety CV113991

| | VALUE | | |
|---|---|---|---|
| CHARACTERISTIC | CV113991 | I226218 | I285291 |
| 4. EAR | | | |
| Silk Color | Green-Yellow | Yellow | Green-Yellow |
| Number Per Stalk | 1.0 | 1.0 | 1.0 |
| Position (attitude) | Upright | Upright | Upright |
| Length cm. | 15.5 | 17.0 | 12.0 |
| Shape | Semi-Conical | Semi-Conical | Semi-Conical |
| Diameter cm. | 4.0 | 4.1 | 3.9 |
| Shank Length cm. | 9.7 | 10.5 | 5.2 |
| Husk Bract | Short | Short | Short |
| Husk Cover cm. | 2.3 | 6.3 | 2.4 |
| Husk Opening | Tight | Tight | Tight |
| Husk Color Fresh | Green | Green | Green |
| Husk Color Dry | Buff | Buff | Buff |
| Cob Diameter cm. | 2.0 | 2.5 | 2.3 |
| Cob Color | Red | Red | Pink |
| Shelling Percent | 89.1 | 83.6 | 87.7 |
| 5. KERNEL | | | |
| Row Number | 18.7 | 14.4 | 14.0 |
| Number Per Row | 26.3 | 27.0 | 18.8 |
| Row Direction | Slightly Curved | Straight | Slightly Curved |
| Type | Dent | Dent | Flint |
| Cap Color | Deep Yellow | Yellow-Orange | Deep Yellow |
| Side Color | Yellow-Orange | Yellow-Orange | Yellow-Orange |
| Length (depth) mm. | 10.4 | 10.3 | 10.6 |
| Width mm. | 7.5 | 8.4 | 8.0 |
| Thickness | 4.9 | 4.9 | 5.4 |
| Endosperm Type | Normal | Normal | Normal |
| Endosperm Color | Pale Yellow | Orange | Orange |

*These are typical values. Values may vary due to environment. Other values that are substantially equivalent are also within the scope of the invention.

C. Deposit Information

A deposit was made of at least 2500 seeds of corn variety CV113991 with the American Type Culture Collection (ATCC), 10801 University Boulevard, Manassas, Va. 20110-2209 USA. The deposit was assigned ATCC Accession No. PTA-121479. The date of deposit of the seeds with the ATCC was Aug. 8, 2014. Access to this deposit will be available during the pendency of the application to the Commissioner of Patents and Trademarks and persons determined by the Commissioner to be entitled thereto upon request. The deposit will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent or under the Plant Variety Protection Act (7 U.S.C. 2321 et seq.).

IV. Further Embodiments of the Invention

In one embodiment, compositions are provided comprising a seed of corn variety CV113991 comprised in plant seed growth media. Plant seed growth media are well known to those of skill in the art and include, but are in no way limited to, soil or synthetic cultivation medium. Advantageously, plant seed growth media can provide adequate physical support for seeds and can retain moisture and/or nutritional components. Examples of characteristics for soils that may be desirable in certain embodiments can be found, for instance, in U.S. Pat. Nos. 3,932,166 and 4,707,176. Synthetic plant cultivation media are also well known in the art and may, in certain embodiments, comprise polymers or hydrogels. Examples of such compositions are described, for example, in U.S. Pat. No. 4,241,537.

In certain further aspects, the invention provides plants modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene. It is understood that a locus introduced by backcrossing may or may not be transgenic in origin, and thus the term backcrossing specifically includes backcrossing to introduce loci that were created by genetic transformation.

Backcrossing methods can be used with the present invention to improve or introduce a trait into a variety. The term backcrossing as used herein refers to the repeated crossing of a hybrid progeny back to one of the parental corn plants. The parental corn plant which contributes the locus or loci for the desired trait is termed the nonrecurrent or donor parent. This terminology refers to the fact that the nonrecurrent parent is used one time in the backcross protocol and therefore does not recur.

The parental corn plant to which the locus or loci from the nonrecurrent parent are transferred is known as the recurrent parent as it is used for several rounds in the backcrossing protocol (Poehlman et al., In: *Breeding Field Crops*, 4th Ed., Iowa State University Press, Ames, Iowa, 132-155; 321-344, 1995; Fehr, *Principles of Cultivar Development*, 1:360-376, 1987; Sprague and Dudley, In: *Corn and Corn Improvement*, 3rd Ed., Crop Science of America, Inc.; Soil Science of America, Inc., Wisconsin. 881-883; 901-918, 1988). In a typical backcross protocol, the original parent of interest (recurrent parent) is crossed to a second variety (nonrecurrent parent) that carries the genetic locus of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the transferred locus from the nonrecurrent parent. The backcross process may be accelerated by the use of genetic markers, such as SSR, RFLP, SNP or AFLP markers to identify plants with the greatest genetic complement from the recurrent parent.

The selection of a suitable recurrent parent is an important step for a successful backcrossing procedure. The goal of a backcross protocol is to add or substitute one or more new traits in the original variety and progeny therefrom. To accomplish this, a genetic locus of the recurrent parent is modified or substituted with the desired locus from the non-recurrent parent, while retaining essentially all of the rest of the desired genetic, and therefore the desired physiological and morphological constitution of the original plant. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, waxy starch, herbicide resistance, resistance for bacterial, fungal, or viral disease, insect resistance, male fertility and enhanced nutritional quality. These genes are generally inherited through the nucleus, but may be inherited through the cytoplasm. Some known exceptions to this are genes for male sterility, some of which are inherited cytoplasmically, but still act as a single locus trait.

Direct selection may be applied where a genetic locus acts as a dominant trait. An example of a dominant trait is the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

Many useful traits are those which are introduced by genetic transformation techniques. Methods for the genetic transformation of corn are known to those of skill in the art. For example, methods which have been described for the genetic transformation of corn include electroporation (U.S. Pat. No. 5,384,253), electrotransformation (U.S. Pat. No. 5,371,003), microprojectile bombardment (U.S. Pat. No. 5,550,318; U.S. Pat. No. 5,736,369, U.S. Pat. No. 5,538,880; and PCT Publication WO 95/06128), Agrobacterium-mediated transformation (U.S. Pat. No. 5,591,616 and E.P. Publication EP672752), direct DNA uptake transformation of protoplasts (Omirulleh et al., *Plant Mol. Biol.,* 21(3):415-428, 1993) and silicon carbide fiber-mediated transformation (U.S. Pat. No. 5,302,532 and U.S. Pat. No. 5,464,765).

It is understood to those of skill in the art that a transgene need not be directly transformed into a plant, as techniques for the production of stably transformed corn plants that pass single loci to progeny by Mendelian inheritance are well known in the art. Such loci may therefore be passed from parent plant to progeny plants by standard plant breeding techniques that are well known in the art. Non-limiting examples of traits that may be introduced into a corn plant according to specific embodiments of the invention are provided below.

A. Male Sterility

Examples of genes conferring male sterility include those disclosed in U.S. Pat. No. 3,861,709, U.S. Pat. No. 3,710,511, U.S. Pat. No. 4,654,465, U.S. Pat. No. 5,625,132, and U.S. Pat. No. 4,727,219, each of the disclosures of which are specifically incorporated herein by reference in their entirety. The use of herbicide-inducible male sterility genes is described in U.S. Pat. No. 6,762,344. Male sterility genes can increase the efficiency with which hybrids are made, in that they eliminate the need to physically emasculate the corn plant used as a female in a given cross.

Where one desires to employ male-sterility systems with a corn plant in accordance with the invention, it may be beneficial to also utilize one or more male-fertility restorer genes. For example, where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the corn plant is utilized, e.g., for silage, but in most cases, the seeds will be deemed the most valuable portion of the crop, so fertility of the hybrids in these crops must be restored. Therefore, one aspect of the current invention concerns plants of the corn variety CV113991 comprising a genetic locus capable of restoring male fertility in an otherwise male-sterile plant. Examples of male-sterility genes and corresponding restorers which could be employed with the plants of the invention are well known to those of skill in the art of plant breeding and are disclosed in, for instance, U.S. Pat. No. 5,530,191; U.S. Pat. No. 5,689,041; U.S. Pat. No. 5,741,684; and U.S. Pat. No. 5,684,242, the disclosures of which are each specifically incorporated herein by reference in their entirety.

B. Herbicide Resistance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for ALS and AHAS enzymes as described, for example, by Lee et al., *EMBO J.,* 7:1241, 1988; Gleen et al., *Plant Molec. Biology,* 18:1185-1187, 1992; and Miki et al., *Theor. Appl. Genet.,* 80:449, 1990.

Resistance genes for glyphosate (resistance conferred by mutant 5-enolpyruvl-3 phosphikimate synthase (EPSPS) and aroA genes, respectively), and hygromycin B phosphotransferase, and to other phosphono compounds such as glufosinate (phosphinothricin acetyl transferase (PAT) and *Streptomyces hygroscopicus* phosphinothricin-acetyl transferase (bar) genes) may also be used. See, for example, U.S. Pat. No. 4,940,835 to Shah, et al., which discloses the nucleotide sequence of a form of EPSPS which can confer glyphosate resistance. Examples of specific EPSPS transformation events conferring glyphosate resistance are provided by U.S. Pat. No. 6,040,497.

A DNA molecule encoding a mutant aroA gene can be obtained under ATCC accession number 39256, and the nucleotide sequence of the mutant gene is disclosed in U.S. Pat. No. 4,769,061 to Comai. A hygromycin B phosphotransferase gene from *E. coli* which confers resistance to glyphosate in tobacco callus and plants is described in Penaloza-Vazquez et al., *Plant Cell Reports,* 14:482-487, 1995. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European patent application No. 0 242 246 to Leemans et al. DeGreef et al. (*Biotechnology,* 7:61, 1989), describe the production of transgenic plants that express chimeric bar genes coding for phosphinothricin acetyl transferase activity. Exemplary genes conferring resistance to phenoxy propionic acids and cycloshexones, such as sethoxydim and haloxyfop, are the Acct-S1, Accl-S2 and Acct-S3 genes described by Marshall et al. (*Theor. Appl. Genet.,* 83:4:35, 1992).

Genes conferring resistance to a herbicide that inhibits photosynthesis are also known, such as a triazine (psbA and gs+ genes) and a benzonitrile (nitrilase gene). Przibila et al. (*Plant Cell,* 3:169, 1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (*Biochem. J.,* 285(Pt 1):173-180, 1992). Protoporphyrinogen oxidase (PPO) is the target of the PPO-inhibitor class of herbicides; a PPO-inhibitor resistant PPO gene was recently identified in *Amaranthus tuberculatus* (Patzoldt et al., *PNAS,* 103(33):12329-2334, 2006). The herbicide methyl viologen inhibits $CO_2$ assimilation. Foyer et al. (*Plant Physiol.,* 109:1047-1057, 1995) describe a plant overexpressing glutathione reductase (GR), which is resistant to methyl viologen treatment.

Siminszky (*Phytochemistry Reviews,* 5:445-458, 2006) describes plant cytochrome P450-mediated detoxification of multiple, chemically unrelated classes of herbicides.

Other examples of herbicide resistance have been described, for instance, in U.S. Pat. Nos. 6,803,501; 6,448,476; 6,248,876; 6,225,114; 6,107,549; 5,866,775; 5,804,425; 5,633,435; 5,463,175.

C. Waxy Starch

The waxy characteristic is an example of a recessive trait. In this example, the progeny resulting from the first backcross generation (BC1) must be grown and selfed. A test is then run on the selfed seed from the BC1 plant to determine which BC1 plants carried the recessive gene for the waxy trait. In other recessive traits additional progeny testing, for example growing additional generations such as the BC1S1, may be required to determine which plants carry the recessive gene.

D. Disease and Pest Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example, Jones et al. (*Science,* 266:7891, 1994) (cloning of the tomato Cf-9 gene for resistance to *Cladosporium fulvum*); Martin et al. (*Science*, 262: 1432, 1993) (tomato Pto gene for resistance to *Pseudomonas syringae* pv. tomato); and Mindrinos et al. (*Cell*, 78(6):1089-1099, 1994) (*Arabidopsis RPS2* gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.*, 28:451, 1990. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al. (*Nature*, 366:469, 1993), who show that transgenic plants expressing recombinant antibody genes are protected from virus attack. Virus resistance has also been described in, for example, U.S. Pat. Nos. 6,617,496; 6,608,241; 6,015,940; 6,013,864; 5,850,023 and 5,304,730. Additional means of inducing whole-plant resistance to a pathogen include modulation of the systemic acquired resistance (SAR) or pathogenesis related (PR) genes, for example, genes homologous to the *Arabidopsis thaliana* NIM1/NPR1/SAI1, and/or by increasing salicylic acid production (Ryals et al., *Plant Cell*, 8:1809-1819, 1996).

Logemann et al. (*Biotechnology*, 10:305, 1992), for example, disclose transgenic plants expressing a barley ribosome-inactivating gene having an increased resistance to fungal disease. Plant defensins may be used to provide resistance to fungal pathogens (Thomma et al., *Planta*, 216:193-202, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; and 6,316,407.

Nematode resistance has been described, for example, in U.S. Pat. No. 6,228,992 and bacterial disease resistance in U.S. Pat. No. 5,516,671.

E. Insect Resistance

One example of an insect resistance gene includes a *Bacillus thuringiensis* (Bt) protein, a derivative thereof or a synthetic polypeptide modeled thereon. See, for example, Geiser et al. (*Gene*, 48(1):109-118, 1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al. (*Plant Molec. Biol.*, 24:25, 1994), who disclose the nucleotide sequences of several *Clivia miniata* mannose-binding lectin genes. A vitamin-binding protein may also be used, such as avidin. See PCT application US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., *J. Biol. Chem.*, 262: 16793, 1987 (nucleotide sequence of rice cysteine proteinase inhibitor); Huub et al., *Plant Molec. Biol.*, 21:985, 1993 (nucleotide sequence of cDNA encoding tobacco proteinase inhibitor I); and Sumitani et al., *Biosci. Biotech. Biochem.*, 57:1243, 1993 (nucleotide sequence of *Streptomyces nitrosporeus* α-amylase inhibitor).

An insect-specific hormone or pheromone may also be used. See, for example, the disclosure by Hammock et al. (*Nature*, 344:458, 1990), of baculovirus expression of cloned juvenile hormone esterase, an inactivator of juvenile hormone; Gade and Goldsworthy (Eds. *Physiological System in Insects*, Elsevier Academic Press, Burlington, Mass., 2007), describing allostatins and their potential use in pest control; and Palli et al., *Vitam. Horm.*, 73:59-100, 2005, disclosing use of ecdysteroid and ecdysteroid receptor in agriculture. The diuretic hormone receptor (DHR) was identified in Price et al. (*Insect Mol. Biol.*, 13:469-480, 2004) as a candidate target of insecticides.

Still other examples include an insect-specific antibody or an immunotoxin derived therefrom and a developmental-arrestive protein. See Taylor et al. (Seventh Int'l Symposium on Molecular Plant-Microbe Interactions, Edinburgh, Scotland, Abstract W97, 1994), who described enzymatic inactivation in transgenic tobacco via production of single-chain antibody fragments. Numerous other examples of insect resistance have been described. See, for example, U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245 and 5,763,241.

F. Modified Fatty Acid, Phytate and Carbohydrate Metabolism

Genes may be used conferring modified fatty acid metabolism, in terms of content and quality. For example, stearyl-ACP desaturase genes may be used. See Knutzon et al., *Proc. Natl. Acad. Sci. USA*, 89:2624, 1992. Various fatty acid desaturases have also been described, such as a *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (McDonough et al., *J. Biol. Chem.*, 267 (9):5931-5936, 1992); a gene encoding a stearoyl-acyl carrier protein delta-9 desaturase from castor (Fox et al. *Proc. Natl. Acad. Sci. USA*, 90(6):2486-2490, 1993); Δ6- and Δ12-desaturases from the cyanobacteria Synechocystis responsible for the conversion of linoleic acid (18:2) to gamma-linolenic acid (18:3 gamma) (Reddy et al., *Plant Mol. Biol.*, 22(2):293-300, 1993); a gene from *Arabidopsis thaliana* that encodes an omega-3 desaturase (Arondel et al., *Science*, 258(5086): 1353-1355 1992); plant Δ9-desaturases (PCT Application Publ. No. WO 91/13972) and soybean and *Brassica* Δ15-desaturases (European Patent Application Publ. No. EP 0616644).

Modified oils production is disclosed, for example, in U.S. Pat. Nos. 6,444,876; 6,426,447 and 6,380,462. High oil production is disclosed, for example, in U.S. Pat. Nos. 6,495,739; 5,608,149; 6,483,008 and 6,476,295. Modified fatty acid content is disclosed, for example, in U.S. Pat. Nos. 6,828,475; 6,822,141; 6,770,465; 6,706,950; 6,660,849; 6,596,538; 6,589,767; 6,537,750; 6,489,461 and 6,459,018.

Phytate metabolism may also be modified by introduction of a phytase-encoding gene to enhance breakdown of phytate, adding more free phosphate to the transformed plant. For example, see Van Hartingsveldt et al., *Gene*, 127:87, 1993, for a disclosure of the nucleotide sequence of an *Aspergillus niger* phytase gene. In corn, this, for example, could be accomplished by cloning and then reintroducing DNA associated with the single allele which is responsible for corn mutants characterized by low levels of phytic acid. See Raboy et al., *Plant Physiol.*, 124(1):355-368, 2000.

A number of genes are known that may be used to alter carbohydrate metabolism. For example, plants may be transformed with a gene coding for an enzyme that alters the branching pattern of starch. See Shiroza et al., *J. Bacteriol.*, 170:810, 1988 (nucleotide sequence of *Streptococcus mutans* fructosyltransferase gene); Steinmetz et al., *Mol. Gen. Genet.*, 20:220, 1985 (nucleotide sequence of *Bacillus subtilis* levansucrase gene); Pen et al., *Biotechnology*, 10:292, 1992 (production of transgenic plants that express *Bacillus licheniformis* α-amylase); U.S. Pat. No. 6,166,292 (low raffinose); Elliot et al., *Plant Molec. Biol.*, 21:515, 1993 (nucleotide sequences of tomato invertase genes); Sergaard et al., *J. Biol. Chem.*, 268:22480, 1993 (site-directed mutagenesis of barley α-amylase gene); Fisher et al., *Plant Physiol.*, 102: 1045, 1993 (maize endosperm starch branching enzyme II); and U.S. Pat. Nos. 6,538,181; 6,538,179; 6,538,178; 5,750,876 and 6,476,295 (starch content). The Z10 gene encoding a 10 kD zein storage protein from maize may also be used to alter the quantities of 10 kD zein in the cells relative to other components (Kirihara et al., *Gene*, 71(2):359-370, 1988).

U.S. Patent Appl. Pub. No. 20030163838 describes maize cellulose synthase genes and methods of use thereof.

G. Resistance to Abiotic Stress

Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis*, respectively, can provide protection against drought (summarized from Annex II Genetic Engineering for Abiotic Stress Tolerance in Plants, Consultative Group On International Agricultural Research Technical Advisory Committee). Overexpression of superoxide dismutase can be used to protect against superoxides, as described in U.S. Pat. No. 5,538,878 to Thomas et al.

H. Additional Traits

Additional traits can be introduced into the corn variety of the present invention. A non-limiting example of such a trait is a coding sequence which decreases RNA and/or protein levels. The decreased RNA and/or protein levels may be achieved through RNAi methods, such as those described in U.S. Pat. No. 6,506,559 to Fire and Mellow.

Another trait that may find use with the corn variety of the invention is a sequence which allows for site-specific recombination. Examples of such sequences include the FRT sequence, used with the FLP recombinase (Zhu and Sadowski, *J. Biol. Chem.*, 270:23044-23054, 1995); and the LOX sequence, used with CRE recombinase (Sauer, *Mol. Cell. Biol.*, 7:2087-2096, 1987). The recombinase genes can be encoded at any location within the genome of the corn plant, and are active in the hemizygous state.

It may also be desirable to make corn plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, *Microbiology & Mol. Biol. Reviews*, 67:16-37, 2003).

In addition to the modification of oil, fatty acid or phytate content described above, it may additionally be beneficial to modify the amounts or levels of other compounds. For example, the amount or composition of antioxidants can be altered. See, for example, U.S. Pat. No. 6,787,618, U.S. Patent Appl. Pub. No. 20040034886 and International Patent Appl. Pub. No. WO 00/68393, which disclose the manipulation of antioxidant levels, and International Patent Appl. Pub. No. WO 03/082899, which discloses the manipulation of a antioxidant biosynthetic pathway.

Additionally, seed amino acid content may be manipulated. U.S. Pat. No. 5,850,016 and International Patent Appl. Pub. No. WO 99/40209 disclose the alteration of the amino acid compositions of seeds. U.S. Pat. Nos. 6,080,913 and 6,127,600 disclose methods of increasing accumulation of essential amino acids in seeds.

U.S. Pat. No. 5,559,223 describes synthetic storage proteins in which the levels of essential amino acids can be manipulated. International Patent Appl. Pub. No. WO 99/29882 discloses methods for altering amino acid content of proteins. International Patent Appl. Pub. No. WO 98/20133 describes proteins with enhanced levels of essential amino acids. International Patent Appl. Pub. No. WO 98/56935 and U.S. Pat. Nos. 6,346,403, 6,441,274 and 6,664,445 disclose plant amino acid biosynthetic enzymes. International Patent Appl. Pub. No. WO 98/45458 describes synthetic seed proteins having a higher percentage of essential amino acids than wildtype.

U.S. Pat. No. 5,633,436 discloses plants comprising a higher content of sulfur-containing amino acids; U.S. Pat. No. 5,885,801 discloses plants comprising a high threonine content; U.S. Pat. Nos. 5,885,802 and 5,912,414 disclose plants comprising high methionine content; U.S. Pat. No. 5,990,389 discloses plants comprising a high lysine content; U.S. Pat. No. 6,459,019 discloses plants comprising an increased lysine and threonine content; International Patent Appl. Pub. No. WO 98/42831 discloses plants comprising a high lysine content; International Patent Appl. Pub. No. WO 96/01905 discloses plants comprising a high threonine content; and International Patent Appl. Pub. No. WO 95/15392 discloses plants comprising a high lysine content.

I. Origin and Breeding History of an Exemplary Introduced Trait

85DGD1 MLms is a conversion of 85DGD1 to cytoplasmic male sterility. 85DGD1 MLms was derived using backcross methods. 85DGD1 (a proprietary inbred of Monsanto Company) was used as the recurrent parent and MLms, a germplasm source carrying ML cytoplasmic sterility, was used as the nonrecurrent parent. The breeding history of the converted inbred 85DGD1 MLms can be summarized as follows:

| | |
|---|---|
| Hawaii Nurseries Planting Date Apr. 02, 1992 | Made up S-O: Female row 585 male row 500 |
| Hawaii Nurseries Planting Date Jul. 15, 1992 | S-O was grown and plants were backcrossed times 85DGD1 (rows 444 ′ 443) |
| Hawaii Nurseries Planting Date Nov. 18, 1992 | Bulked seed of the BC1 was grown and backcrossed times 85DGD1 (rows V3-27 ′ V3-26) |
| Hawaii Nurseries Planting Date Apr. 02, 1993 | Bulked seed of the BC2 was grown and backcrossed times 85DGD1 (rows 37 ′ 36) |
| Hawaii Nurseries Planting Date Jul. 14, 1993 | Bulked seed of the BC3 was grown and backcrossed times 85DGD1 (rows 99 ′ |

-continued

| | |
|---|---|
| Hawaii Nurseries Planting Date Oct. 28, 1993 | 98) Bulked seed of BC4 was grown and backcrossed times 85DGD1 (rows KS-63 ´ KS-62) |
| Summer 1994 | A single ear of the BC5 was grown and backcrossed times 85DGD1 (MC94-822 ´ MC94-822-7) |
| Winter 1994 | Bulked seed of the BC6 was grown and backcrossed times 85DGD1 (3Q-1 ´ 3Q-2) |
| Summer 1995 | Seed of the BC7 was bulked and named 85DGD1 MLms. |

J. Illustrative Procedures for Introduction of a Desired Trait

As described above, techniques for the production of corn plants with added traits are well known in the art (see, e.g., Poehlman et al., In: *Breeding Field Crops*, 4th Ed., Iowa State University Press, Ames, Iowa, 132-155; 321-344, 1995; Fehr, *Principles of Cultivar Development*, 1:360-376, 1987; Sprague and Dudley, In: *Corn and Corn Improvement*, 3rd Ed., Crop Science of America, Inc.; Soil Science of America, Inc., Wisconsin. 881-883; 901-918, 1988). A non-limiting example of such a procedure one of skill in the art would use for preparation of a corn plant of CV113991 comprising an added trait is as follows:

(a) crossing corn plant CV113991 to a second (nonrecurrent) corn plant comprising a locus to be converted in corn plant CV113991;

(b) selecting at least a first progeny plant resulting from the crossing and comprising the locus;

(c) crossing the selected progeny to corn plant CV113991; and (d) repeating steps (b) and (c) until a plant of variety CV113991 is obtained comprising the locus.

Following these steps, essentially any locus may be introduced into corn variety CV113991. For example, molecular techniques allow introduction of any given locus, without the need for phenotypic screening of progeny during the backcrossing steps.

PCR™ and Southern hybridization are two examples of molecular techniques that may be used for confirmation of the presence of a given locus and thus conversion of that locus. The techniques are carried out as follows: Seeds of progeny plants are grown and DNA isolated from leaf tissue (see Sambrook et al., In: *Molecular cloning*, Cold Spring Harbor Laboratory Press, Cold Spring Harbor, N.Y., 2001; Shure et al., *Cell*, 35(1):225-233, 1983). Approximately one gram of leaf tissue is lyophilized overnight in 15 ml polypropylene tubes. Freeze-dried tissue is ground to a powder in the tube using a glass rod. Powdered tissue is mixed thoroughly with 3 ml extraction buffer (7.0 M urea, 0.35 M NaCl, 0.05 M Tris-HCl pH 8.0, 0.01 M EDTA, 1% sarcosine). Tissue/buffer homogenate is extracted with 3 ml phenol/chloroform. The aqueous phase is separated by centrifugation, and precipitated twice using 1/10 volume of 4.4 M ammonium acetate, pH 5.2, and an equal volume of isopropanol. The precipitate is washed with 75% ethanol and resuspended in 100-500 µl TE (0.01 M Tris-HCl, 0.001 M EDTA, pH 8.0). The DNA may then be screened as desired for presence of the locus.

For PCR™, 200-1000 ng genomic DNA from the progeny plant being screened is added to a reaction mix containing 10 mM Tris-HCl, pH 8.3, 1.5 mM $MgCl_2$, 50 mM KCl, 0.1 mg/ml gelatin, 200 µM each dATP, dCTP, dGTP, dTTP, 20% glycerol, 2.5 units Taq DNA polymerase and 0.5 µM each of forward and reverse DNA primers that span a segment of the locus being converted. The reaction is run in a thermal cycling machine 3 minutes at 94 C, 39 repeats of the cycle 1 minute at 94 C, 1 minute at 50 C, 30 seconds at 72° C., followed by 5 minutes at 72° C. Twenty µl of each reaction mix is run on a 3.5% NuSieve gel in TBE buffer (90 mM Tris-borate, 2 mM EDTA) at 50V for two to four hours. The amplified fragment is detected using an agarose gel. Detection of an amplified fragment corresponding to the segment of the locus spanned by the primers indicates the presence of the locus.

For Southern analysis, plant DNA is restricted, separated in an agarose gel and transferred to a Nylon filter in 10×SCP (20 SCP: 2 M NaCl, 0.6 M disodium phosphate, 0.02 M disodium EDTA) according to standard methods (Southern, *J. Mol. Biol.*, 98:503-517, 1975). Locus DNA or RNA sequences are labeled, for example, radioactively with $^{32}P$ by random priming (Feinberg & Vogelstein, *Anal. Biochem.*, 132(1):6-13, 1983). Filters are prehybridized in 6×SCP, 10% dextran sulfate, 2% sarcosine, and 500 µg/ml denatured salmon sperm DNA. The labeled probe is denatured, hybridized to the filter and washed in 2×SCP, 1% SDS at 65° C. for 30 minutes and visualized by autoradiography using Kodak XAR5 film. Presence of the locus is indicated by detection of restriction fragments of the appropriate size.

V. Tissue Cultures and In Vitro Regeneration of Corn Plants

A further aspect of the invention relates to tissue cultures of the corn plant designated CV113991. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, kernels, ears, cobs, leaves, husks, stalks, roots, root tips, anthers, silk, and the like. In a preferred embodiment, the tissue culture comprises embryos, protoplasts, meristematic cells, pollen, leaves or anthers derived from immature tissues of these plant parts. Means for preparing and maintaining plant tissue cultures are well known in the art (U.S. Pat. No. 5,538,880; and U.S. Pat. No. 5,550,318, each incorporated herein by reference in their entirety). By way of example, a tissue culture comprising organs such as tassels or anthers has been used to produce regenerated plants (U.S. Pat. No. 5,445, 961 and U.S. Pat. No. 5,322,789; the disclosures of which are incorporated herein by reference).

One type of tissue culture is tassel/anther culture. Tassels contain anthers which in turn enclose microspores. Microspores develop into pollen. For anther/microspore culture, if tassels are the plant composition, they are preferably selected at a stage when the microspores are uninucleate, that is, include only one, rather than 2 or 3 nuclei. Methods to determine the correct stage are well known to those skilled in the art and include mitramycin fluorescent staining (Pace et al., *Theoretical and Applied Genetics*, 73:863-869, 1987), trypan blue (preferred) and acetocarmine squashing. The mid-uninucleate microspore stage has been found to be the developmental stage most responsive to the subsequent methods disclosed to ultimately produce plants.

Although microspore-containing plant organs such as tassels can generally be pretreated at any cold temperature below about 25° C., a range of 4 to 25° C. is preferred, and a range of 8 to 14° C. is particularly preferred. Although other temperatures yield embryoids and regenerated plants, cold temperatures produce optimum response rates compared to pretreatment at temperatures outside the preferred range. Response rate is measured as either the number of embryoids or the number of regenerated plants per number of microspores initiated in culture. Exemplary methods of microspore culture are disclosed in, for example, Gaillard et al., *Plant Cell Reports*, 10(2):55, 1991, and U.S. Pat. No. 5,322,789 and U.S. Pat. No 5,445,961, the disclosures of which are specifically incorporated herein by reference.

Although not required, when tassels are employed as the plant organ, it is generally preferred to sterilize their surface. Following surface sterilization of the tassels, for example, with a solution of calcium hypochloride, the anthers are removed from about 70 to 150 spikelets (small portions of the tassels) and placed in a preculture or pretreatment medium. Larger or smaller amounts can be used depending on the number of anthers.

When one elects to employ tassels directly, tassels are preferably pretreated at a cold temperature for a predefined time, preferably at 10° C. for about 4 days. After pretreatment of a whole tassel at a cold temperature, dissected anthers are further pretreated in an environment that diverts microspores from their developmental pathway. The function of the pre-culture medium is to switch the developmental program from one of pollen development to that of embryoid/callus development. An embodiment of such an environment in the form of a preculture medium includes a sugar alcohol, for example mannitol or sorbitol, inositol or the like. An exemplary synergistic combination is the use of mannitol at a temperature of about 10° C. for a period ranging from about 10 to 14 days. In a preferred embodiment, 3 ml of 0.3 M mannitol combined with 50 mg/l of ascorbic acid, silver nitrate, and colchicine is used for incubation of anthers at 10° C. for between 10 and 14 days. Another embodiment is to substitute sorbitol for mannitol. The colchicine produces chromosome doubling at this early stage. The chromosome doubling agent is preferably only present at the preculture stage.

It is believed that the mannitol or other similar carbon structure or environmental stress induces starvation and functions to force microspores to focus their energies on entering developmental stages. The cells are unable to use, for example, mannitol as a carbon source at this stage. It is believed that these treatments confuse the cells causing them to develop as embryoids and plants from microspores. Dramatic increases in development from these haploid cells, as high as 25 embryoids in $10^4$ microspores, have resulted from using these methods.

To isolate microspores, an isolation media is preferred. An isolation media is used to separate microspores from the anther walls while maintaining their viability and embryogenic potential. An illustrative embodiment of an isolation media includes a 6% sucrose or maltose solution combined with an antioxidant such as 50 mg/l of ascorbic acid, 0.1 mg/l biotin, and 400 mg/l of proline, combined with 10 mg/l of nicotinic acid and 0.5 mg/l $AgNO_3$. In another embodiment, the biotin and proline are omitted.

An isolation media preferably has a higher antioxidant level where it is used to isolate microspores from a donor plant (a plant from which a plant composition containing a microspore is obtained) that is field grown in contrast to greenhouse grown. A preferred level of ascorbic acid in an isolation medium is from about 50 mg/l to about 125 mg/l and, more preferably, from about 50 mg/l to about 100 mg/l.

One can find particular benefit in employing a support for the microspores during culturing and subculturing. Any support that maintains the cells near the surface can be used. An illustrative embodiment of a solid support is a TRAN-SWELL® culture dish. Another embodiment of a solid support for development of the microspores is a bilayer plate wherein liquid media is on top of a solid base. Other embodiments include a mesh or a millipore filter. Preferably, a solid support is a nylon mesh in the shape of a raft. A raft is defined as an approximately circular support material which is capable of floating slightly above the bottom of a tissue culture vessel, for example, a petri dish, of about a 60 or 100 mm size, although any other laboratory tissue culture vessel will suffice. In an illustrative embodiment, a raft is about 55 mm in diameter.

Culturing isolated microspores on a solid support, for example, on a 10 mm pore nylon raft floating on 2.2 ml of medium in a 60 mm petri dish, prevents microspores from sinking into the liquid medium and thus avoiding low oxygen tension. These types of cell supports enable the serial transfer of the nylon raft with its associated microspore/embryoids ultimately to full strength medium containing activated charcoal and solidified with, for example, GELRITE™ (solidifying agent).

The liquid medium passes through the mesh while the microspores are retained and supported at the medium-air interface. The surface tension of the liquid medium in the petri dish causes the raft to float. The liquid is able to pass through the mesh; consequently, the microspores stay on top. The mesh remains on top of the total volume of liquid medium.

The culture vessels can be further defined as either (1) a bilayer 60 mm petri plate wherein the bottom 2 ml of medium are solidified with 0.7% agarose overlaid with 1 mm of liquid containing the microspores; (2) a nylon mesh raft wherein a wafer of nylon is floated on 1.2 ml of medium and 1 ml of isolated microspores is pipetted on top; or (3) TRAN-SWELL® plates wherein isolated microspores are pipetted onto membrane inserts which support the microspores at the surface of 2 ml of medium.

Examples of processes of tissue culturing and regeneration of corn are described in, for example, European Patent Application 0 160 390, Green and Rhodes, *Maize for Biological Research*, 367-372, 1982; and Duncan et al., *Planta*, 165: 322-332, 1985; Songstad et al., *Plant Cell Reports*, 7:262-265, 1988; Rao et al., In: *Somatic Embryogenesis in Glume Callus Cultures*, Maize Genetics Cooperation Newsletter #60, 1986; Conger et al., *Plant Cell Reports*, 6:345-347, 1987; PCT Application WO 95/06128, Armstrong and Green, *Planta*, 164:207-214, 1985; Gordon-Kamm et al., The Plant Cell, 2:603-618, 1990; Gaillard et al., *Plant Cell Reports*, 10(2):55, 1991; and U.S. Pat. No. 5,736,369.

VI. Processes of Crossing Corn Plants and the Corn Plants Produced by Such Crosses The present invention provides processes of preparing novel corn plants and corn plants produced by such processes. In accordance with such a process, a first parent corn plant may be crossed with a second parent corn plant wherein at least one of the first and second corn plants is the inbred corn plant CV113991. One application of the process is in the production of $F_1$ hybrid plants. Another important aspect of this process is that it can be used for the development of novel inbred lines. For example, the inbred corn plant CV113991 could be crossed to any second plant, and the resulting hybrid progeny each selfed for about 5 to 7 or more generations, thereby providing a large number of distinct, pure-breeding inbred lines. These inbred lines could then be crossed with other inbred or non-inbred lines and the resulting hybrid progeny analyzed for beneficial characteristics. In this way, novel inbred lines conferring desirable characteristics could be identified.

Corn plants (*Zea mays* L.) can be crossed by either natural or mechanical techniques. Natural pollination occurs in corn when wind blows pollen from the tassels to the silks that protrude from the tops of the recipient ears. Mechanical pollination can be effected either by controlling the types of pollen that can blow onto the silks or by pollinating by hand. In one embodiment, crossing comprises the steps of:
  (a) planting in pollinating proximity seeds of a first and a second parent corn plant, and preferably, seeds of a first inbred corn plant and a second, distinct inbred corn plant;
  (b) cultivating or growing the seeds of the first and second parent corn plants into plants that bear flowers;
  (c) emasculating flowers of either the first or second parent corn plant, i.e., treating the flowers so as to prevent pollen production, or alternatively, using as the female parent a male sterile plant, thereby providing an emasculated parent corn plant;
  (d) allowing natural cross-pollination to occur between the first and second parent corn plants;
  (e) harvesting seeds produced on the emasculated parent corn plant; and, where desired,
  (f) growing the harvested seed into a corn plant, preferably, a hybrid corn plant.

Parental plants are typically planted in pollinating proximity to each other by planting the parental plants in alternating rows, in blocks or in any other convenient planting pattern. Where the parental plants differ in timing of sexual maturity, it may be desired to plant the slower maturing plant first, thereby ensuring the availability of pollen from the male parent during the time at which silks on the female parent are receptive to pollen. Plants of both parental parents are cultivated and allowed to grow until the time of flowering. Advantageously, during this growth stage, plants are in general treated with fertilizer and/or other agricultural chemicals as considered appropriate by the grower.

At the time of flowering, in the event that plant CV113991 is employed as the male parent, the tassels of the other parental plant are removed from all plants employed as the female parental plant to avoid self-pollination. The detasseling can be achieved manually but also can be done by machine, if desired. Alternatively, when the female parent corn plant comprises a cytoplasmic or nuclear gene conferring male sterility, detasseling may not be required. Additionally, a chemical gametocide may be used to sterilize the male flowers of the female plant. In this case, the parent plants used as the male may either not be treated with the chemical agent or may comprise a genetic factor which causes resistance to the emasculating effects of the chemical agent. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904, the disclosure of which is specifically incorporated herein by reference in its entirety. Furthermore, the use of glyphosate herbicide to produce male sterile corn plants is disclosed in U.S. Pat. No. 6,762,344 and PCT Publication WO 98/44140.

Following emasculation, the plants are then typically allowed to continue to grow and natural cross-pollination occurs as a result of the action of wind, which is normal in the pollination of grasses, including corn. As a result of the emasculation of the female parent plant, all the pollen from the male parent plant is available for pollination because tassels, and thereby pollen bearing flowering parts, have been previously removed from all plants of the inbred plant being used as the female in the hybridization. Of course, during this hybridization procedure, the parental varieties are grown such that they are isolated from other corn fields to minimize or prevent any accidental contamination of pollen from foreign sources. These isolation techniques are well within the skill of those skilled in this art.

Both parental inbred plants of corn may be allowed to continue to grow until maturity or the male rows may be destroyed after flowering is complete. Only the ears from the female inbred parental plants are harvested to obtain seeds of a novel $F_1$ hybrid. The novel $F_1$ hybrid seed produced can then be planted in a subsequent growing season in commercial fields or, alternatively, advanced in breeding protocols for purposes of developing novel inbred lines.

Alternatively, in another embodiment of the invention, both first and second parent corn plants can be from variety CV113991. Thus, any corn plant produced using corn plant CV113991 forms a part of the invention. As used herein, crossing can mean selfing, backcrossing, crossing to another or the same inbred, crossing to populations, and the like. All corn plants produced using the inbred corn plant CV113991 as a parent are, therefore, within the scope of this invention.

A. $F_1$ Hybrid Corn Plant and Seed Production

One beneficial use of the instant corn variety is in the production of hybrid seed. Any time the inbred corn plant CV113991 is crossed with another, different, corn inbred, a first generation ($F_1$) corn hybrid plant is produced. As such, an $F_1$ hybrid corn plant can be produced by crossing CV113991 with any second inbred maize plant. Essentially any other corn plant can be used to produce a hybrid corn plant having corn plant CV113991 as one parent. All that is required is that the second plant be fertile, which corn plants naturally are, and that the plant is not corn variety CV113991.

The goal of the process of producing an $F_1$ hybrid is to manipulate the genetic complement of corn to generate new combinations of genes which interact to yield new or improved traits (phenotypic characteristics). A process of producing an $F_1$ hybrid typically begins with the production of one or more inbred plants. Those plants are produced by repeated crossing of ancestrally related corn plants to try to combine certain genes within the inbred plants.

Corn has a diploid phase which means two conditions of a gene (two alleles) occupy each locus (position on a chromosome). If the alleles are the same at a locus, there is said to be homozygosity. If they are different, there is said to be heterozygosity. In a completely inbred plant, all loci are homozygous. Because many loci when homozygous are deleterious to the plant, in particular leading to reduced vigor, less kernels, weak and/or poor growth, production of inbred plants is an unpredictable and arduous process. Under some conditions, heterozygous advantage at some loci effectively bars perpetuation of homozygosity.

A single cross hybrid corn variety is the cross of two inbred plants, each of which has a genotype which complements the genotype of the other. Typically, $F_1$ hybrids are more vigorous than their inbred parents. This hybrid vigor, or heterosis, is manifested in many polygenic traits, including markedly improved yields, better stalks, better roots, better uniformity and better insect and disease resistance. In the development of hybrids only the $F_1$ hybrid plants are typically sought. An $F_1$ single cross hybrid is produced when two inbred plants are crossed. A double cross hybrid is produced from four inbred plants crossed in pairs (A×B and C×D) and then the two $F_1$ hybrids are crossed again (A×B)×(C×D).

Thousands of corn varieties are known to those of skill in the art, any one of which could be crossed with corn plant CV113991 to produce a hybrid plant. For example, the U.S. Patent & Trademark Office has issued more than 300 utility patents for corn varieties. Estimates place the number of different corn accessions in gene banks around the world at around 50,000 (Chang, In *Plant Breeding in the* 1990s, Stalker and Murphy (Eds.), Wallingford, U.K., CAB International, 17-35, 1992). The Maize Genetics Cooperation Stock Center, which is supported by the U.S. Department of Agriculture, has a total collection approaching 80,000 individually pedigreed samples (www.maizecoop.cropsci.uiuc.edu/).

An example of an $F_1$ hybrid which has been produced with CV113991 as a parent is the hybrid CH909736. Hybrid CH909736 was produced by crossing inbred corn plant CV113991 with the inbred corn plant designated CV995128 (U.S. Pat. No. 8,319,066, the disclosure of which is specifically incorporated herein by reference in its entirety).

When the inbred corn plant CV113991 is crossed with another inbred plant to yield a hybrid, it can serve as either the maternal or paternal plant. For many crosses, the outcome is the same regardless of the assigned sex of the parental plants. Depending on the seed production characteristics relative to a second parent in a hybrid cross, it may be desired to use one of the parental plants as the male or female parent. Some plants produce tighter ear husks leading to more loss, for example due to rot. There can be delays in silk formation which deleteriously affect timing of the reproductive cycle for a pair of parental plants. Seed coat characteristics can be preferable in one plant. Pollen can be shed better by one plant. Therefore, a decision to use one parent plant as a male or female may be made based on any such characteristics as is well known to those of skill in the art.

B. Development of Corn Varieties

The development of new varieties using one or more starting varieties is well known in the art. In accordance with the invention, novel varieties may be created by crossing corn variety CV113991 followed by multiple generations of breeding according to such well known methods. New varieties may be created by crossing corn variety CV113991 with any second plant. In selecting such a second plant to cross for the purpose of developing novel inbred lines, it may be desired to choose those plants which either themselves exhibit one or more selected desirable characteristics or which exhibit the desired characteristic(s) when in hybrid combination. Examples of potentially desired characteristics include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Once initial crosses have been made with corn variety CV113991, inbreeding takes place to produce new inbred varieties. Inbreeding requires manipulation by human breeders. Even in the extremely unlikely event inbreeding rather than crossbreeding occurred in natural corn, achievement of complete inbreeding cannot be expected in nature due to well known deleterious effects of homozygosity and the large number of generations the plant would have to breed in isolation. The reason for the breeder to create inbred plants is to have a known reservoir of genes whose gametic transmission is predictable.

The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. After at least five generations, the inbred plant is considered genetically pure.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The development of a hybrid corn variety involves three steps: (1) the selection of plants from various germplasm pools; (2) the selfing of the selected plants for several generations to produce a series of inbred plants, which, although different from each other, each breed true and are highly uniform; and (3) crossing the selected inbred plants with unrelated inbred plants to produce the hybrid progeny ($F_1$). During the inbreeding process in corn, the vigor of the plants decreases. Vigor is restored when two unrelated inbred plants are crossed to produce the hybrid progeny ($F_1$). An important consequence of the homozygosity and homogeneity of the inbred plants is that the hybrid between any two inbreds is always the same. Once the inbreds that give a superior hybrid have been identified, hybrid seed can be reproduced indefinitely as long as the homogeneity of the inbred parents is maintained. Conversely, much of the hybrid vigor exhibited by $F_1$ hybrids is lost in the next generation ($F_2$). Consequently, seed from hybrid varieties is not used for planting stock. It is not generally beneficial for farmers to save seed of $F_1$ hybrids. Rather, farmers purchase $F_1$ hybrid seed for planting every year.

The development of inbred plants generally requires at least about 5 to 7 generations of selfing. Inbred plants are then cross-bred in an attempt to develop improved $F_1$ hybrids. Hybrids are then screened and evaluated in small scale field trials. Typically, about 10 to 15 phenotypic traits, selected for their potential commercial value, are measured. A selection index of the most commercially important traits is used to help evaluate hybrids. FACT, an acronym for Field Analysis Comparison Trial (strip trials), is an on-farm experimental testing program employed by Monsanto Company to perform the final evaluation of the commercial potential of a product.

During the next several years, a progressive elimination of hybrids occurs based on more detailed evaluation of their phenotype. Eventually, strip trials (FACT) are conducted to formally compare the experimental hybrids being developed with other hybrids, some of which were previously developed and generally are commercially successful. That is, comparisons of experimental hybrids are made to competitive hybrids to determine if there was any advantage to further development of the experimental hybrids. Examples of such comparisons are presented herein below. After FACT testing is complete, determinations may be made whether commercial development should proceed for a given hybrid.

C. $F_1$ Hybrid Comparisons

As mentioned above, hybrids are progressively eliminated following detailed evaluations of their phenotype, including formal comparisons with other commercially successful hybrids. Strip trials are used to compare the phenotypes of hybrids grown in as many environments as possible. They are performed in many environments to assess overall performance of the new hybrids and to select optimum growing conditions.

Because the corn is grown in close proximity, environmental factors that affect gene expression, such as moisture, temperature, sunlight, and pests, are minimized. For a decision to be made to commercialize a hybrid, it is not necessary that the hybrid be better than all other hybrids. Rather, significant improvements must be shown in at least some traits that would create improvements in some niches.

Examples of such comparative data are set forth herein below in Table 2, which presents a comparison of performance data for a hybrid made with CV113991 as one parent, versus selected hybrids of commercial value.

TABLE 2

Comparative Data for CH909736, a Hybrid Having CV113991 as One Inbred Parent

| Entries Compared | YLD_BE | MST | STLP | RTLP | FNSP | SDV | PHT | EHT | TWT | STG |
|---|---|---|---|---|---|---|---|---|---|---|
| CH909736 | 194.7 | 17 | 1.8 | 0.8 | 99.3 | 3 | 84 | 40 | 57.5 | 5.2 |
| DKC50-67 | 178.9 | 15.4 | 4 | 1.7 | 95.1 | 3.4 | 87 | 39 | 58 | 5.8 |
| Deviation | 15.88 | 1.56 | −2.22 | −0.86 | 4.17 | −0.44 | −3.04 | 1.76 | −0.57 | −0.62 |
| Significance | ** | ** | ** |  | ** | ** | ** | * | ** | ** |
| CH909736 | 189 | 17.1 | 1.8 | 0.7 | 99.2 | 3 | 83 | 40 | 57.2 | 4.7 |
| DKC52-62 | 184.3 | 16.6 | 3.3 | 3.1 | 98.4 | 3.3 | 83 | 41 | 57.3 | 5.4 |
| Deviation | 4.72 | 0.51 | −1.46 | −2.38 | 0.84 | −0.21 | −0.32 | −1.37 | −0.07 | −0.77 |
| Significance | ** | ** | ** |  | * |  | * |  |  | ** |

Significance levels are indicated as:
+ = 10%,
* = 5%,
** = 1%
LEGEND ABBREVIATIONS:
YLD_B = Yield (bushels/acre)
MST = Moisture
STLP = Stalk Lodging (percent)
RTLP = Root Lodging (percent)
FNSP = Final Stand (percent of test mean)
SDV = Seedling Vigor Rating
PHT = Plant Height (inches)
EHT = Ear Height (inches)
TWT = Test Weight (pounds)
STG = Staygreen Rating
GSPP = Greensnap (percentage)
GDU = GDUs to Shed
SLK = GDUs to Silk D. Physical Description of $F_1$ Hybrids The present invention provides $F_1$ hybrid corn plants derived from the corn plant CV113991. The physical characteristics of an exemplary hybrid produced using CV113991 as one inbred parent are set forth in Table 3. An explanation of terms used in Table 3 can be found in the Definitions, set forth hereinabove.

TABLE 3

Morphological Traits for CH909736, a Hybrid Having CV113991 as One Inbred Parent

| | CHARACTERISTIC | VALUE |
|---|---|---|
| 1. | STALK | |
| | Plant Height cm. | 240.8 |
| | Ear Height cm. | 86.4 |
| | Anthocyanin | Absent |
| | Brace Root Color | Faint |
| | Internode Direction | Straight |
| | Internode Length cm. | 16.6 |
| 2. | LEAF | |

TABLE 3-continued

Morphological Traits for CH909736, a Hybrid Having CV113991 as One Inbred Parent

| | CHARACTERISTIC | VALUE |
|---|---|---|
| | Color | Dark Green |
| | Length cm. | 85.9 |
| | Width cm. | 10.6 |
| | Sheath Anthocyanin | Weak |
| | Sheath Pubescence | Moderate |
| | Marginal Waves | Moderate |
| | Longitudinal Creases | Many |
| 3. | TASSEL | |
| | Length cm. | 41.7 |
| | Peduncle Length cm. | 10.0 |
| | Branch Number | 8.6 |

TABLE 3-continued

Morphological Traits for CH909736, a Hybrid Having CV113991 as One Inbred Parent

| | CHARACTERISTIC | VALUE |
|---|---|---|
| | Anther Color | Yellow |
| | Glume Color | Green |
| | Glume Band | Absent |
| 4. | EAR | |
| | Silk Color | Green-Yellow |
| | Number Per Stalk | 1.0 |
| | Position | Upright |
| | Length cm. | 17.7 |
| | Shape | Semi-Conical |
| | Diameter cm. | 4.6 |
| | Shank Length cm. | 5.6 |
| | Husk Bract | Short |
| | Husk Opening | Tight |
| | Husk Cover cm. | 2.3 |
| | Husk Color Fresh | Green |
| | Husk Color Dry | Buff |
| | Cob Diameter cm. | 2.5 |
| | Cob Color | Red |

TABLE 3-continued

Morphological Traits for CH909736, a Hybrid
Having CV113991 as One Inbred Parent

| | CHARACTERISTIC | VALUE |
|---|---|---|
| | Shelling Percent | 88.4 |
| 5. | KERNEL | |
| | Row Number | 15.6 |
| | Number Per Row | 35.4 |
| | Row Direction | Straight |
| | Type | Dent |
| | Cap Color | Yellow |
| | Side Color | Yellow |
| | Length (depth) mm. | 12.7 |
| | Width mm. | 8.5 |
| | Thickness | 4.4 |
| | Endosperm Type | Normal |
| | Endosperm Color | Yellow |

*These are typical values. Values may vary due to environment. Other values that are substantially equivalent are also within the scope of the invention.

VII. Genetic Complements

The present invention provides a genetic complement of the inbred corn plant variety designated CV113991. Further provided by the invention is a hybrid genetic complement, wherein the complement is formed by the combination of a haploid genetic complement from CV113991 and another haploid genetic complement. Means for determining such a genetic complement are well-known in the art.

As used herein, the phrase "genetic complement" means an aggregate of nucleotide sequences, the expression of which defines the phenotype of a corn plant or a cell or tissue of that plant. By way of example, a corn plant is genotyped to determine a representative sample of the inherited markers it possesses. Markers are alleles at a single locus. They are preferably inherited in codominant fashion so that the presence of both alleles at a diploid locus is readily detectable, and they are free of environmental variation, i.e., their heritability is 1. This genotyping is preferably performed on at least one generation of the descendant plant for which the numerical value of the quantitative trait or traits of interest are also determined. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence or size of a repeated sequence. Heterozygosity refers to different conditions of the gene at a locus. A preferred type of genetic marker for use with the invention is simple sequence repeats (SSRs), although potentially any other type of genetic marker could be used, for example, restriction fragment length polymorphisms (RFLPs), amplified fragment length polymorphisms (AFLPs), single nucleotide polymorphisms (SNPs), and isozymes.

A genetic marker profile of an inbred may be predictive of the agronomic traits of a hybrid produced using that inbred. For example, if an inbred of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data is disclosed in U.S. Pat. No. 5,492,547, the disclosure of which is specifically incorporated herein by reference in its entirety. Such predictions may be made using any suitable genetic marker, for example, SSRs, RFLPs, AFLPs, SNPs, or isozymes.

SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR™), thereby eliminating the need for labor-intensive Southern hybridization. The PCR™ detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology. Following amplification, markers can be scored by gel electrophoresis of the amplification products. Scoring of marker genotype is based on the size (number of base pairs) of the amplified segment.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The references cited herein, to the extent that they provide exemplary procedural or other details supplementary to those set forth herein, are specifically incorporated herein by reference.

What is claimed is:

1. A plant of corn variety CV113991, wherein a sample of seed of corn variety CV113991 has been deposited under ATCC Accession No. PTA-121479.

2. A plant part of the plant of claim 1.

3. The plant part of claim 2, further defined as pollen, an ovule or a cell.

4. A seed of corn variety CV113991, wherein a sample of seed of corn variety CV113991 has been deposited under ATCC Accession No. PTA-121479.

5. The seed of claim 4, further comprising a transgene, wherein the transgene was introduced into corn variety CV113991 by backcrossing or genetic transformation.

6. A composition comprising the seed of claim 4 comprised in plant seed growth media, wherein a sample of seed of corn variety CV113991 has been deposited under ATCC Accession No. PTA-121479.

7. The composition of claim 6, wherein the growth media is soil or a synthetic cultivation medium.

8. An $F_1$ hybrid seed produced by crossing a plant of corn variety CV113991 according to claim 1 with a second, distinct corn plant.

9. The $F_1$ hybrid seed of claim 8, wherein said plant of corn variety CV113991 comprises a transgene that is inherited by the seed, wherein the transgene was introduced into corn variety CV113991 by backcrossing or genetic transformation.

10. An F$_1$ hybrid plant grown from the seed of claim 8.

11. A plant produced by introducing a single locus conversion into corn variety CV113991, or a selfed progeny thereof, wherein the single locus was introduced into corn variety CV113991 by backcrossing or genetic transformation, wherein the plant comprises the single locus conversion and otherwise comprises essentially all of the characteristics of corn variety CV113991, and wherein a sample of seed of corn variety CV113991 has been deposited under ATCC Accession No. PTA-121479.

12. The plant of claim 11, wherein the single locus conversion comprises a transgene.

13. A seed that produces the plant of claim 11.

14. The seed of claim 13, wherein the single locus confers a trait selected from the group consisting of male sterility, herbicide tolerance, insect or pest resistance, disease resistance, modified fatty acid metabolism, abiotic stress resistance, altered seed amino acid composition, site-specific genetic recombination, and modified carbohydrate metabolism.

15. The seed of claim 13, wherein the herbicide tolerance trait is tolerance to an herbicide selected from the group consisting of glyphosate, sulfonylurea, imidazalinone, dicamba, glufosinate, phenoxy proprionic acid, cycloshexone, triazine, benzonitrile, PPO-inhibitor herbicides and broxynil.

16. A method of producing a seed of a progeny plant derived from the corn variety CV113991, the method comprising crossing a plant of corn variety CV113991 according to claim 1 with a corn plant of a second variety to produce at least a first seed.

17. The method of claim 16, further comprising the steps of
   (a) crossing a plant grown from said seed with itself or a second plant to produce a seed of a progeny plant of a subsequent generation;
   (b) growing a progeny plant of a subsequent generation from said seed and crossing the progeny plant of a subsequent generation with itself or a second plant; and
   (c) repeating steps (a) and (b) with sufficient inbreeding until a seed of an inbred corn plant derived from the corn variety CV113991 is produced.

18. The method of claim 17, further comprising crossing said inbred corn plant derived from the corn variety CV113991 with a corn plant of a different genotype to produce seed of a hybrid plant derived from the corn variety CV113991.

19. A method of producing a commodity plant product, the method comprising obtaining the plant of claim 10 or a part thereof and producing said commodity plant product therefrom.

20. The method of claim 19, wherein the commodity plant product is grain, starch, seed oil, corn syrup, or protein.

* * * * *